(12) United States Patent
Ting

(10) Patent No.: US 6,949,091 B2
(45) Date of Patent: Sep. 27, 2005

(54) METHOD FOR INSERTING SOLID OBJECT INTO SKIN

(76) Inventor: Pin Huang Ting, P.O. Box 4-67, Hsin Chuang, Taipei (TW), 242

( * ) Notice: Subject to any disclaimer, the term of this patent is extended or adjusted under 35 U.S.C. 154(b) by 0 days.

(21) Appl. No.: 10/717,847

(22) Filed: Nov. 17, 2003

(65) Prior Publication Data

US 2005/0107768 A1 May 19, 2005

(51) Int. Cl.[7] ............................................. A61M 31/00
(52) U.S. Cl. ........................................ 604/506; 604/59
(58) Field of Search .......................... 604/890.1, 891.1, 604/19, 36, 38, 500, 502, 506, 514, 518–519, 521–522, 48, 93.01, 57–64, 218, 232, 235, 285

(56) References Cited

U.S. PATENT DOCUMENTS

| | | | | |
|---|---|---|---|---|
| 3,757,781 A | * | 9/1973 | Smart | 604/59 |
| 3,780,735 A | * | 12/1973 | Crouter et al. | 604/59 |
| 4,402,308 A | * | 9/1983 | Scott | 604/60 |
| 4,416,659 A | * | 11/1983 | Simpson et al. | 604/48 |
| 4,451,253 A | * | 5/1984 | Harman | 604/60 |
| 4,900,304 A | * | 2/1990 | Fujioka et al. | 604/60 |
| 4,950,234 A | * | 8/1990 | Fujioka et al. | 604/60 |
| 5,277,912 A | * | 1/1994 | Lowe et al. | 604/57 |

* cited by examiner

Primary Examiner—Nicholas D. Lucchesi
Assistant Examiner—Michael M Thompson
(74) Attorney, Agent, or Firm—Charles E. Baxley

(57) ABSTRACT

A method may be used to insert or to engage solid objects into human bodies, and includes a syringe having a bore and a front opening to receive the solid objects. The syringe may then be engaged into the human bodies, and may then be disengaged from the human bodies, to allow the solid objects to be retained within the human bodies after the syringe is disengaged from the human bodies. It is preferable that an extension is extended from the solid objects, and/or bent relative to the solid objects, to retain the solid objects within the human bodies. The solid objects may include a material, such as a fluid or powder medicine received within a capsule.

1 Claim, 5 Drawing Sheets a method in accordance with the present invention is provided for injecting or inserting solid objects into or through skin of patients or users.

METHOD FOR INSERTING SOLID OBJECT INTO SKIN

BACKGROUND OF THE INVENTION

1. Field of the Invention

The present invention relates to a method, and more particularly to a method for injecting or inserting solid objects into or through skin of patients or users.

2. Description of the Prior Art

Typical subcutaneous or hypodermic injections are provided for injecting fluid medicines, with such as syringes, through or into skin of patients or users, or into muscles, blood vessels, etc., for allowing the fluid medicines to flow to the affected parts of the patients or users. The typical syringes may not be used for injecting or inserting solid objects into or through skin of patients or users.

Due to quickly circulation and absorption by patients or users, some of the medicines have been packaged within capsules and then inserted into or through the skin of patients or users. The skin of patients or users is normally required to be cut to form a slot therein, for inserting the solid capsules into or through the skin of patients or users.

Similarly, for inserting the other solid objects, such as pacer makers, into or through the skin of patients or users, it is also required to cut and to form a groove or a slot in the skin of patients or users, in order to engage or to insert the solid objects into or through the skin of patients or users.

After the solid objects have been engaged or inserted into or through the skin of patients or users, the skin is required to be sutured with sutures, in order to retain the solid objects within the patients or users. It is thus difficult and inconvenient and time consuming to insert the solid objects into the patients or users.

The present invention has arisen to mitigate and/or obviate the afore-described disadvantages of the conventional methods for inserting solid objects into patients or users.

SUMMARY OF THE INVENTION

The primary objective of the present invention is to provide a method for injecting or inserting solid objects into or through skin of patients or users without cutting the patients or users.

In accordance with one aspect of the invention, there is provided a method for inserting solid objects into human bodies, the method comprising providing a syringe having a bore and a front opening formed therein, to receive the solid objects therein, engaging the syringe into the human bodies, and disengaging the syringe from the human bodies, to retain the solid objects within the human bodies.

It is preferable that an extension is extended from the solid objects, and/or bent relative to the solid objects, to retain the solid objects within the human bodies while or after the syringe is disengaged from the human bodies.

The solid objects may include a capsule, and a material, such as a fluid or powder medicine received within the capsule, to allow the fluid or powder medicine to be engaged into the human bodies by the help of the capsule.

A plunger may further be provided and engaged into the syringe, to help engage the solid objects into the human bodies.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
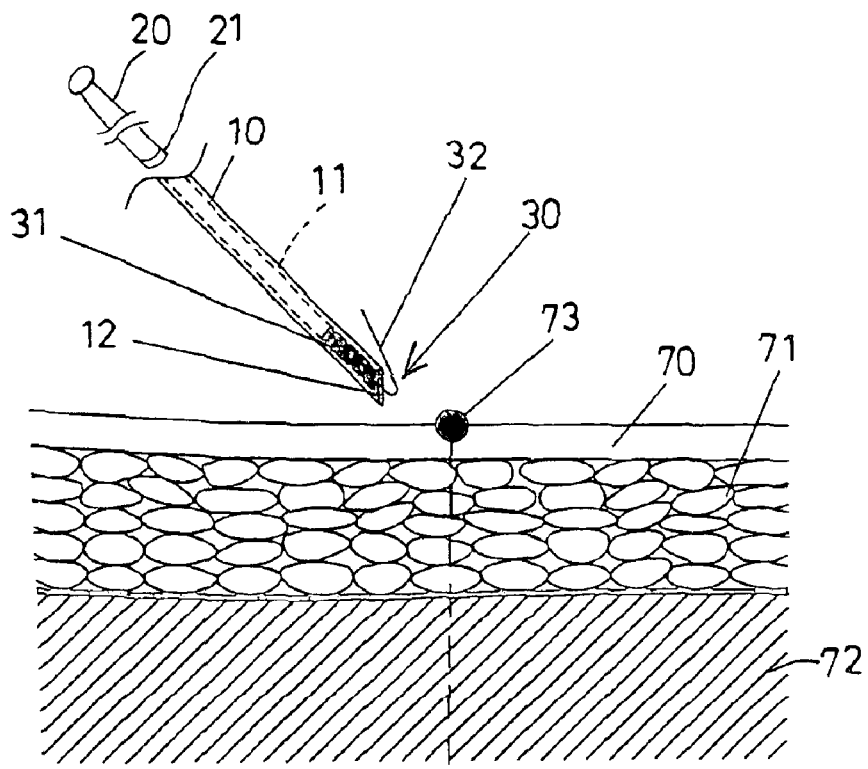
FIG. 1 is a plan schematic view illustrating a method in accordance with the present invention for injecting or inserting solid objects into or through skin of patients or users without cutting the patients or users.

Referring to the drawings, and initially to FIG. 1, a method in accordance with the present invention is provided for injecting or inserting solid objects 30 into or through skin of patients or users, such as for injecting or inserting the solid objects 30 through the stratum corneum 70 and into the stratum spinosum or the stratum granulosum 71 of the epidermis of the patients or users, or into the dermis 72 of the patients or users.

Figure 2:
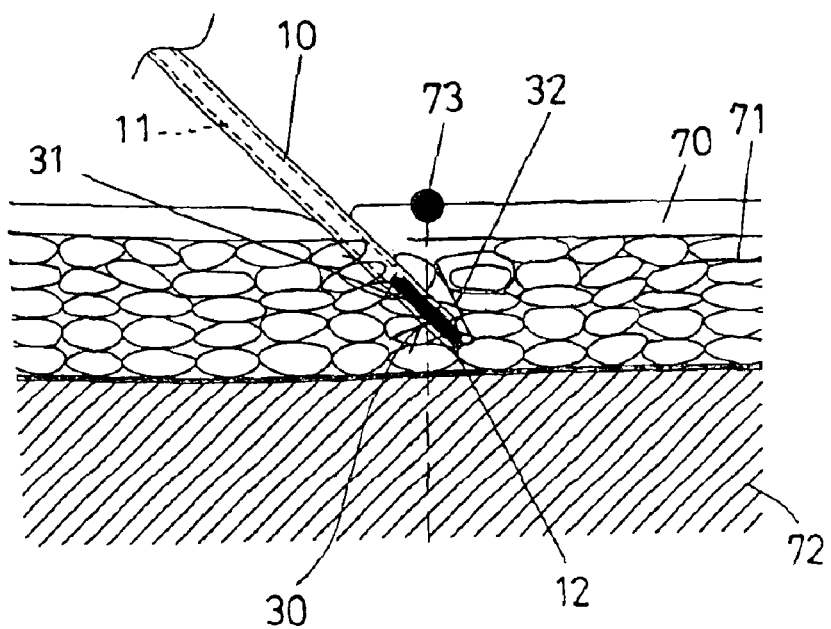
FIGS. 2, 3, 4, 5, 6 are plan schematic views similar to FIG. 1, illustrating a method in accordance with the present invention for injecting or inserting various kinds of solid objects into or through skin of patients or users.
Figure 3:
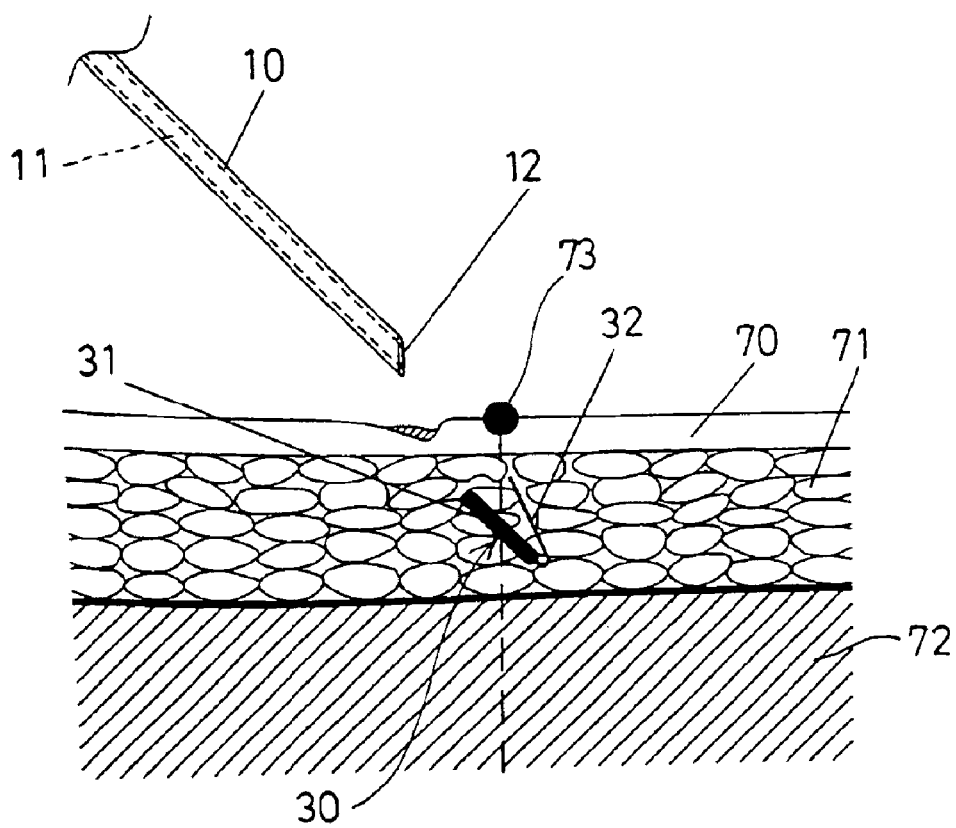

As best shown in FIGS. 1–3, it is preferable that some of the solid objects 30 are preferably injected or inserted into the portions or areas or lines where the acupuncture points 73 are located and where acupuncture needles (not shown) are normally engaged into the human bodies.

The solid objects 30 may be selected from long acting slow releasing solid drug, slow releasing tablets, pace makers, threads in subcutaneous caves, contrast media, etc., capsules for receiving fluid or powder medicines, etc., or slow releasing agents, such as a polymer of nitroglycerin and CATGUT, a polymer of conjugated estradiol and VICRYL, a polymer of metildigoxin and DEXON, etc., or goat intestines for engaging into the portions or areas or lines where the acupuncture points 73 are located.

A syringe 10 includes a bore 11 formed therein and a front opening 12 formed therein and communicating with the bore 11 thereof for receiving the solid objects 30 to be injected or inserted or engaged into the human bodies. A plunger 20 is slidably engaged in the bore 11 of the syringe 10, and includes a piston 21 for helping or facilitating the injection or engagement of the solid objects 30 into the human bodies.

The syringe 10 may be made of various kinds of materials that will not be rejected or excluded by the skin of the human bodies, such as porcelain materials, metal materials, composite materials, plastic materials, and polymers including glyceric acid, lactic acid, etc.

As shown in FIGS. 1–3, the solid objects 30 may comprise a solid object body or member 31 that may be engaged into the bore 11 of the syringe 10 via the front opening 12 of the syringe 10, and/or may comprise an extension 32 extended and bent from the solid object member 31 and preferably bent and located outside the syringe 10.

In operation, the solid objects 30 may be injected or inserted or engaged into the human bodies by injecting or inserting or engaging the plunger 20 into the human bodies, such as engaged through the stratum corneum 70, and into the stratum spinosum or the stratum granulosum 71 of the epidermis, or into the dermis 72 of the patients or users, and/or into the portions where the acupuncture points 73 are located. It is preferable that the syringe 10 includes a length greater than 50 μm, for allowing the syringe 10 to be engaged at least through the stratum corneum 70 of the patients or users.

When the plunger 20 is pulled out of the human bodies, as shown in FIG. 3, the bent extension 32 of the solid object 30 may engage with the human bodies, and thus may retain and maintain the solid object 30 within the human bodies. The solid objects 30 which have the bent extension 32 extended therefrom may thus be engaged into the human bodies without the plunger 20.

Figure 4:
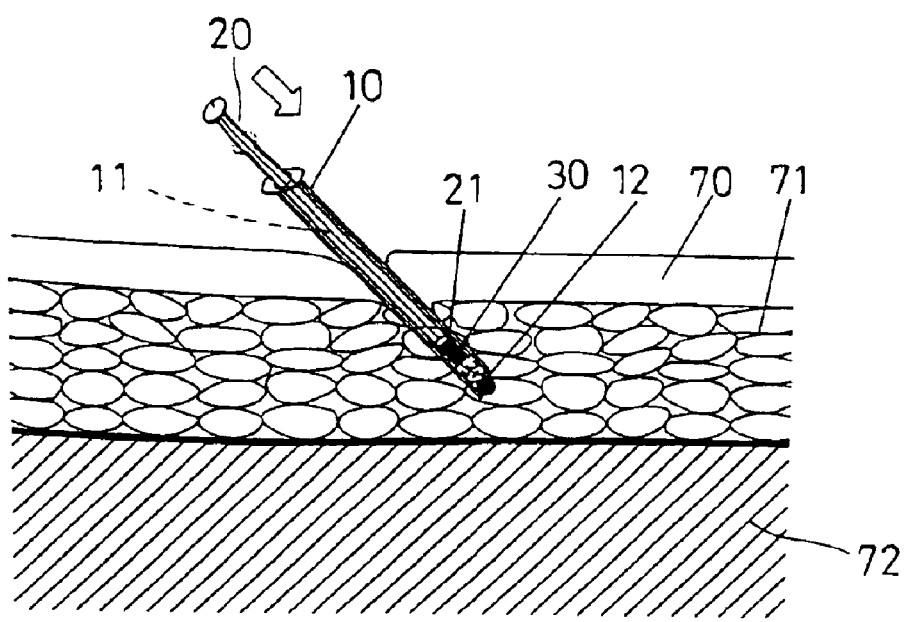
Figure 5:
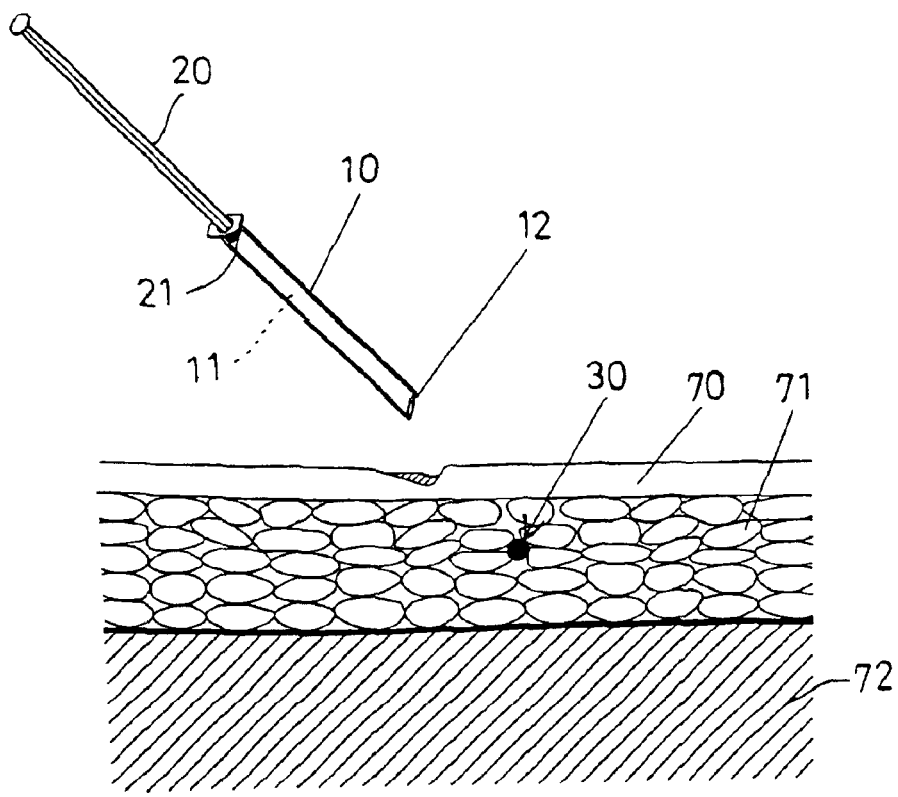

As shown in FIGS. 4 and 5, the solid objects 30 which have no bent extensions extended therefrom may also be engaged into the bore 11 of the syringe 10 via the front opening 12 of the syringe 10, and may be injected or engaged into the human bodies by moving or forcing the plunger 20 along the bore 11 of the syringe 10.

Figure 6:
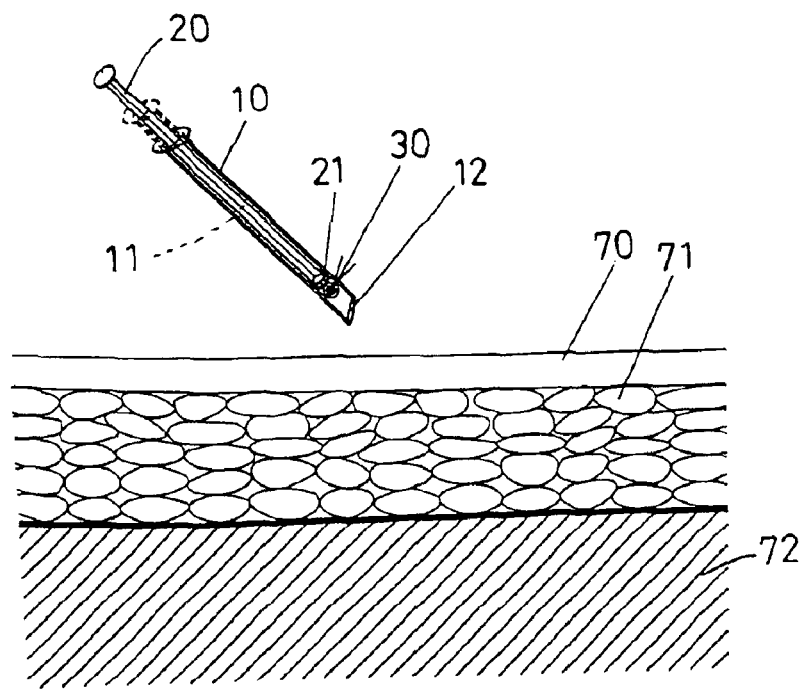
Figure 8:
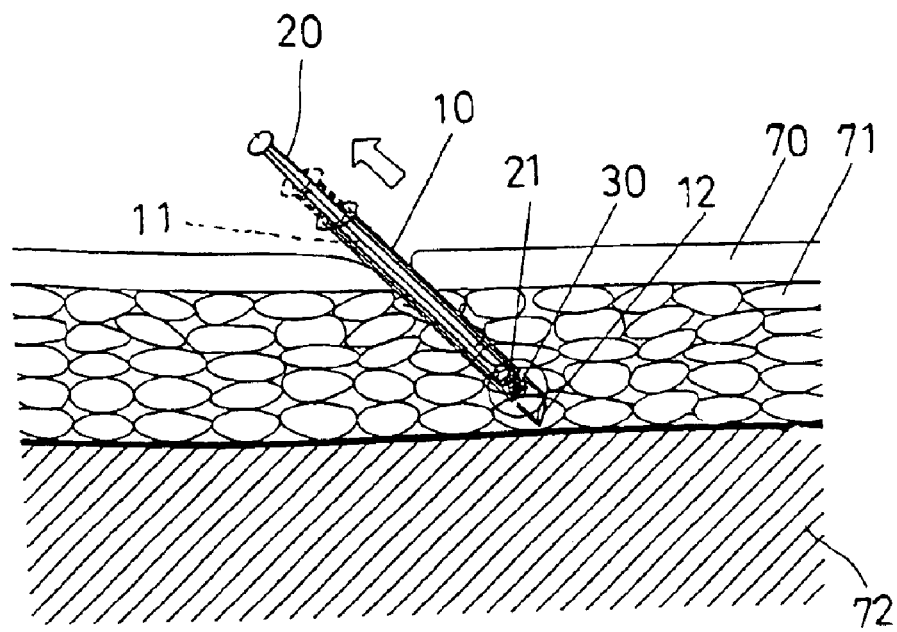
FIGS. 8 and 9 are plan schematic views similar to FIGS. 1–6, illustrating the method for injecting or inserting the solid objects as shown in FIG. 7 into or through skin of patients or users.
Figure 7:
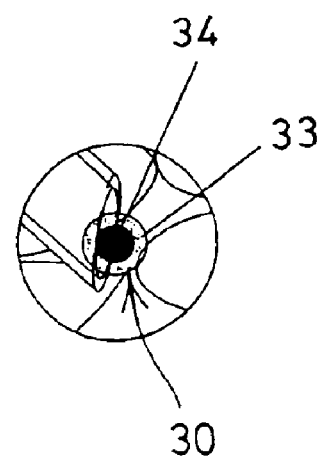
FIG. 7 is an enlarged partial perspective view illustrating a solid object to be injected or inserted into the patients or users.

Referring next to FIGS. 6–9, the solid objects 30 may include a outer film or capsule, such as a gelatine capsule 33 that may be resolved and absorbed by human bodies, and that may be engaged into the bore 11 of the syringe 10 via the front opening 12 of the syringe 10, and that may include a fluid material or medicine or other material 34 received within the capsule 33, such as the normal saline solution, silica gel, or other fluid or powder medicines, best shown in FIG. 7.

In operation, the capsule 33 of the solid object 30 is engaged into the bore 11 of the syringe 10 via the front opening 12 of the syringe 10, and the plunger 20 may move the capsule 33 of the solid object 30 toward the front opening 12 of the syringe 10, in order to retain the solid object 30 within the bore 11 of the syringe 10 and located close to the front opening 12 of the syringe 10, best shown in FIG. 6.

When either of the polymers of the slow releasing agents is selected and injected into the skin of the users, the slow releasing agents may be gradually released into the bodies of the users. For example, the polymer of nitroglycerin and CATGUT may be gradually released into the bodies of the users for more than three (3) weeks, the polymer of conjugated estradiol and VICRYL may be gradually release into the bodies of the users for up to one month, and the polymer of metildigoxin and DEXON may be gradually released into the bodies of the users for more than one month. The pace makers are normally required to be changed or replaced with the new ones every half a year, or every year.

Figure 9:
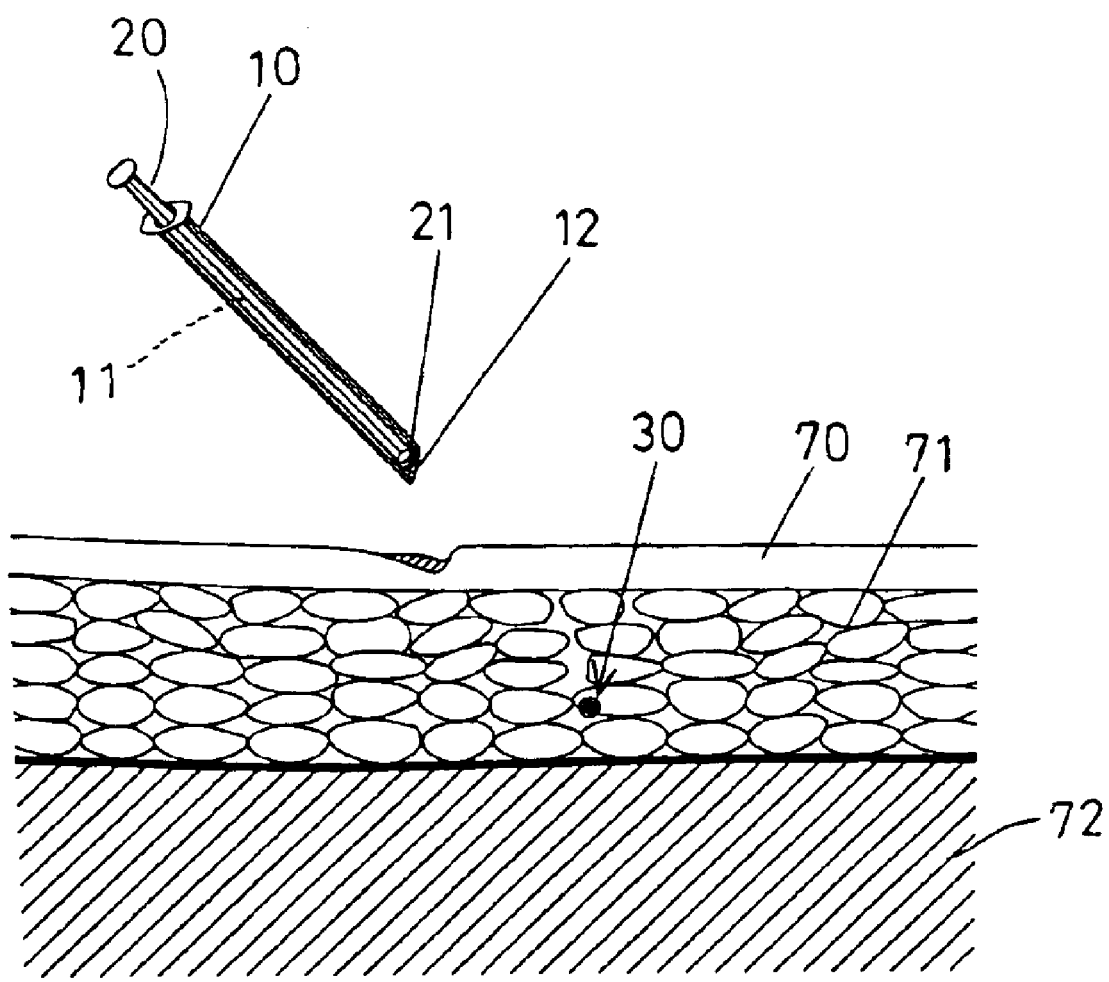

The capsule 33 of the solid object 30 may then be easily injected or engaged into the human bodies by injecting or engaging the syringe 10 into the human bodies (FIG. 8), and may be retained within the human bodies by pulling the syringe 10 out of the human bodies, and by maintaining the plunger 20 in position relative to the human bodies, i.e., by moving the syringe 10 relative to the plunger 20, to allow the solid object 30 to be retained and maintained within the human bodies, FIG. 9.

The medicine 34 may thus be injected or engaged into the human bodies without cutting the patients or users, and the medicine 34 received within the capsule 33 may thus be slow released into the human bodies, in order to prolong the effectiveness of the medicine 34 to the human bodies.

Accordingly, the method of the present invention may be provided for injecting or inserting solid objects into or through skin of patients or users without cutting the patients or users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A method for inserting solid objects into human bodies, said method comprising:

providing a syringe having a bore and a front opening formed therein, to receive the solid objects therein, providing an extension extended from the solid objects and bent relative to the solid objects, to have the extension bent and located outside the syringe, providing a material within a capsule of the solid objects, engaging the syringe into skin of the human bodies, providing and engaging a plunger into the syringe, to help engage the solid objects into the skin of the human bodies, and disengaging the syringe from the human bodies, to retain the solid objects within the human bodies, and the extension of the solid objects being provided to retain the solid objects within the skin of the human bodies after the syringe is disengaged from the human bodies.

* * * * *